United States Patent
Ollivier et al.

(10) Patent No.: US 6,190,635 B1
(45) Date of Patent: *Feb. 20, 2001

(54) PURIFICATION OF THE HYDROCHLORIC ACID BY-PRODUCT OF THE SYNTHESIS OF METHANESULPHONIC ACID

(75) Inventors: Jean Ollivier, Arudy; Rene Clair, Martigues; Denise Molines, Saint-Genis Laval; Marc Ferrigno, Billere, all of (FR)

(73) Assignee: Elf Atochem S.A., Putueax (FR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/126,102

(22) Filed: Jul. 30, 1998

(30) Foreign Application Priority Data

Jul. 31, 1997 (FR) .................................................. 97 09779

(51) Int. Cl.[7] .............................. C01B 7/07; C07C 309/04
(52) U.S. Cl. ................ 423/488; 423/240 R; 423/243.01; 423/245.02; 562/120
(58) Field of Search ............................... 423/488, 243.01, 423/245.2, 240 R; 562/120, 124

(56) References Cited

U.S. PATENT DOCUMENTS

| 2,416,467 | * | 2/1947 | Carney | 423/488 |
| 3,931,289 | * | 1/1976 | Bundy | 560/53 |
| 4,280,966 | | 7/1981 | Hubenett | 423/488 |
| 4,549,993 | * | 10/1985 | McElligott | 562/828 |
| 4,859,373 | * | 8/1989 | Ollivier | 562/119 |

FOREIGN PATENT DOCUMENTS

| 0 675 106 | * | 10/1995 | (EP) . |
| 0 675 107 A1 | | 10/1995 | (EP) . |
| 740242 | | 11/1955 | (GB) . |
| 1 350 328 | | 4/1974 | (GB) . |

OTHER PUBLICATIONS

Search Report, Dated Apr. 6, 1998.

* cited by examiner

*Primary Examiner*—Ngoc-Yen Nguyen
(74) *Attorney, Agent, or Firm*—Smith Gambrell & Russell, LLP

(57) ABSTRACT

In order to remove the methanesulphonyl chloride entrained by the gaseous HCl by-product, an amount of water ranging from 0.01 to 20%, relative to the mass of HCl to be treated, is injected into the HCl gas flow and the temperature is lowered to a value below or equal to 15° C.

4 Claims, 1 Drawing Sheet

PURIFICATION OF THE HYDROCHLORIC ACID BY-PRODUCT OF THE SYNTHESIS OF METHANESULPHONIC ACID

FIELD OF THE INVENTION

The present invention concerns the field of methanesulphonic acid (referred to hereinbelow as MSA) and relates more particularly to a process for the purification of the hydrochloric acid by-product of the synthesis of MSA.

BACKGROUND OF THE INVENTION

The synthesis of MSA from methyl mercaptan and chlorine according to the reaction:

$$CH_3SH + 3\ Cl_2 + 3\ H_2O \rightarrow CH_3SO_3H + 6\ HCl$$

produces a large amount of hydrochloric acid by-product. The HCl gas flow separates from the reaction medium, entraining some of the volatile compounds, and this entrainment is proportionately larger when the reaction is carried out at 100° C. By means known per se, the chlorine and the methyl mercaptan are readily eliminated from the hydrochloric acid. The water is not a hindrance since the aim is to recover a 33% solution of HCl in water.

However, during the reaction which leads to methanesulphonic acid, a relatively volatile intermediate is produced, methylsulphonyl chloride $CH_3SO_2Cl$ (MSC), which, on working up the gaseous HCl with water, converts into methanesulphonic acid, thereby contaminating the hydrochloric solution and making it unsuitable for a certain number of applications.

The entrainment of MSC is considerable since the contact between the HCl and the MSC takes place at high temperature. The excess MSC is readily removed using the known standard techniques such as, for example washing the hydrochloric effluent with the MSA produced in the reaction and preferably purified. Nerveless, appreciable amounts of MSC are entrained by the HCl since the operations do not take place at low temperature, but in the region of room temperature. It is known that depending on the temperature (see Table I), the MSC content of the hydrochloric acid takes increasing values.

TABLE I

| Temperature (° C.) | MSC in HCl gas (ppm) | MSA in aqueous 33% HCl (ppm) |
|---|---|---|
| −5 | 728 | 203 |
| 0 | 1245 | 350 |
| 5 | 1770 | 495 |
| 8 | 2570 | 720 |
| 12 | 4610 | 1290 |
| 15 | 5440 | 1520 |
| 18 | 7120 | 1990 |
| 21 | 8830 | 2470 |

In a usual process for the synthesis of MSA, the HCl flow is at a temperature in the region of 20° C. It thus contains from 5000 to 9000 ppm of MSC, which lead to a 33% hydrochloric solution containing from 1500 to 2500 ppm of MSA.

BRIEF SUMMARY OF THE INVENTION

The aim of the present invention is to. provide a process which makes it possible to reduce the MSC content in the HCl gas as much as possible, without making it necessary to use extremely low temperatures or highly sophisticated and expensive techniques.

BRIEF DESCRIPTION OF THE DRAWING

The single FIGURE is a diagram of the apparatus in accordance with the invention.

DETAILED DESCRIPTION OF THE INVENTION

Figure 1:
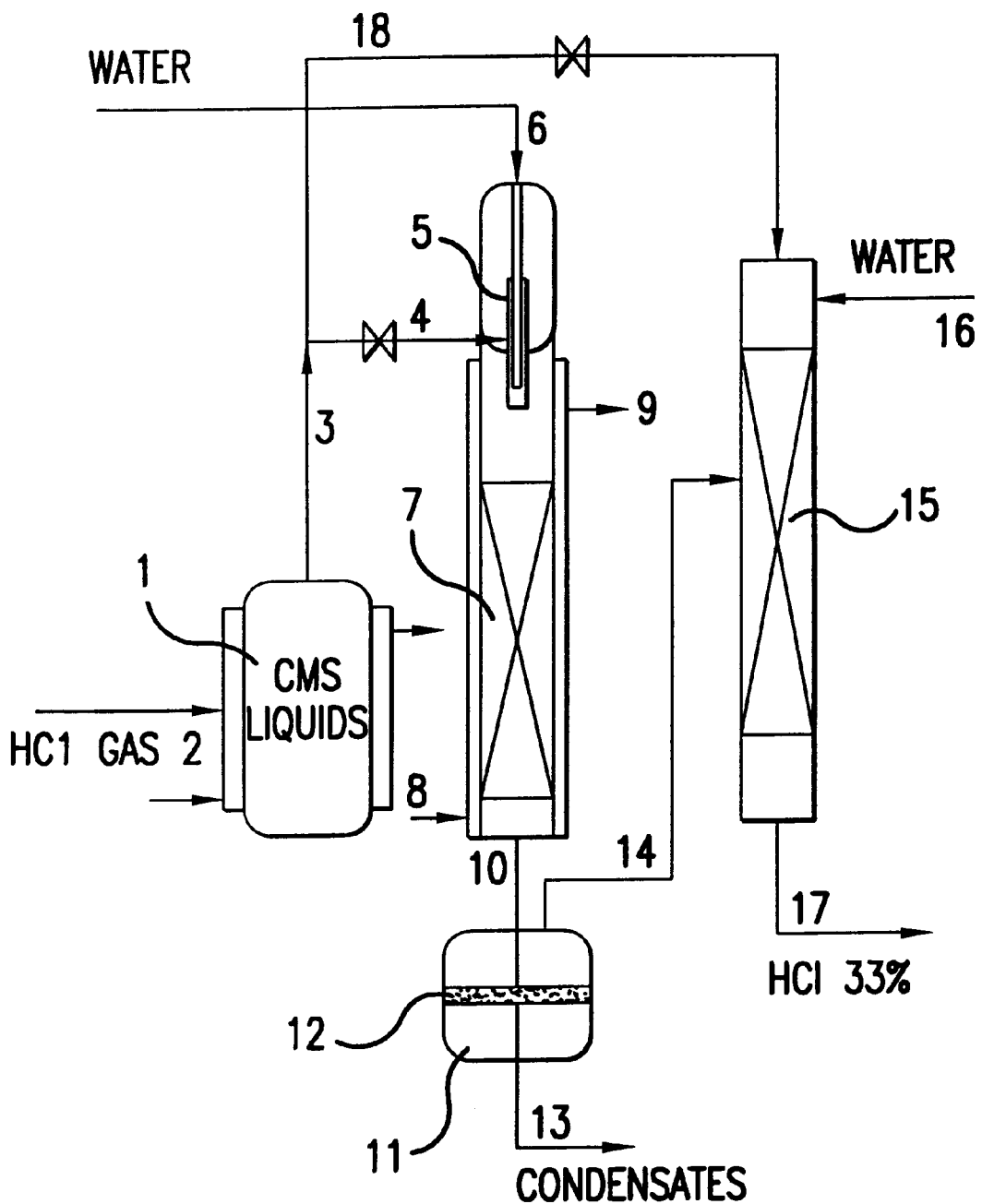

According to the invention, this result is achieved by a process which consists essentially in bringing the temperature of the HCl gas flow to. a value below or equal to 15° C. and in injecting into the flow an amount of water ranging from 0.01 to 20% relative to the mass of HCl to be treated.

The cooling and water injection operations can be carried out simultaneously or successively. In the latter case, the water is preferably injected first and cooling carried out thereafter.

In accordance with the process according to the invention, the lowering of the HCl gas temperature to a value below or equal to 15° C., preferably approximately between −5 and +5° C., makes it possible to decrease the MSC content considerably. Thus, for example, the gas cooled from 21° C. to 0° C. goes from a content of 8830 ppm of MSC to a content of 1245 ppm, i.e. an efficacy of 86% or a reduction factor equal to 7.

In accordance with the second characteristic of the process according to the invention, an aerosol of pure water is injected into the hydrochloric gas in an amount corresponding to a few per cent of the mass of HCl to be treated (0.01 to 20%, preferably 5 to 10%). The aggregation effect between the hydrochloric acid and the water which results therefrom makes it possible to trap out most of the residual MSC, which can be returned to the MSA synthesis reactor. Thus, with 10% water relative to the HCl, it is easy to go from an MSC content of 1245 ppm to 120 ppm, i.e. for the process an overall purification efficacy of 98.6% or a reduction factor equal to 73.6. The process according to the invention makes it possible not only to purify the HCl but also to recover more than 17 tonnes of MSC per 1000 tonnes of MSA produced.

The example which follows illustrates the invention without limiting it.

EXAMPLE

Apparatus

The device described in the single figure attached was used. This device, designed to treat 60 litres/hour of hydrochloric gas (about 90 g/h) is made of glass with connecting pipes made of PTFE. Pure MCS was used as the fluid for saturating the HCl.

A stream (2) of HCl gas is passed through the saturator (1) containing liquid MSC and the exiting stream of HCl charged with MSC is conveyed via the pipes (3) and (4) to a treatment column containing three main parts, namely:

- a gas injector (5) containing a water-spraying system (mini hydro-injector) supplied at (6) by a syringe pump or by a peristaltic micropump,
- a heat-exchange zone (7) consisting of a coil (8 and 9) through which a coolant liquid runs, and
- a retention zone (11) separated from the rest of the column by a splash head (12) made of rock wool packed to a thickness of 5 centimetres and prewashed with concentrated hydrochloric acid, rinsed with distilled water and dried with ether before being inserted.

After passage through the heat-exchange zone (7), the hydrochloric acid and the condensates are conveyed via the pipe (10) to the retention zone (11). The condensates leave via the pipe (13). The hydrochloric acid crosses the splash head (12) and is conveyed via the pipe (14) to a column (15) for working up the purified HCl gas with water. This standard column (15), supplied with water via the pipe (16), is thermostatically regulated and operates in batchwise mode in order to produce at (17) hydrochloric acid with a titre of about 33%.

The same column was used to control the MSC titre of the contaminated HCl to be treated, by circulating the flow of HCl gas charged with MSC directly from the saturator (1) to the column (15) via the pipes (3) and (18).

Procedure

Anhydrous hydrochloric acid gas was diffused into liquid MSC whose temperature was set so as to charge the HCl with the desired amount of MSC vapour. After passing into the treatment column, the hydrochloric gas was worked up with water so as to obtain a solution at a concentration of 33% by mass. The MSC entrained by the HCl was hydrolysed into MSA, which was assayed according to the known analytical techniques.

The results obtained are given in the table below.

TABLE II

| Tests | ppm MSC in HCl gas | Condensation temperature (° C.) | Water added to HCl (%) | ppm MSC in HCl gas treated | Operation yield (%) |
| --- | --- | --- | --- | --- | --- |
| 1 | 1775 | 0 | — | 1245 | 30 |
| 2 | 1775 | 0 | 12 | 24 | 98.6 |
| 3 | 2250 | 0 | — | 1245 | 44.6 |
| 4 | 2250 | 0 | 6 | 25 | 98.9 |
| 5 | 4610 | 0 | — | 1245 | 72 |
| 6 | 4610 | 0 | 10 | 270 | 94 |
| 7 | 5440 | 0 | — | 1245 | 77 |
| 8 | 5440 | 0 | 10 | 140 | 97.4 |
| 9 | 7120 | 5 | — | 1770 | 75 |
| 10 | 7120 | 5 | 10 | 250 | 96.4 |
| 11 | 6830 | −5 | — | 730 | 91 |
| 12 | 8830 | 0 | 10 | 80 | 99 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. Process for purification of the HCl gas by-product of the synthesis of methanesulphonic acid, wherein methanesulphonic chloride entrained by the HCl gas is removed, comprising:

a) injecting an amount of water ranging from 0.01 to 20%, relative to the mass of HCl to be treated, into a flow of the HCl gas;

b) lowering the temperature of the flow of the HCl gas to a value from −5° C. to 15° C. to form a purified HCl gas and condensates containing the methanesulfonyl chloride; and c) separating the purified HCl gas from the condensates.

2. Process according to claim 1, wherein 5 to 10% of water, relative to the mass of HCl to be treated is injected.

3. Process for purification of HCl gas by-product of the synthesis of methanesulphonic acid, wherein methanesulphonyl chloride entrained in the HCl gas is removed, comprising:

a) injecting an amount of water ranging from 5%–10%, relative to the mass of HCl to be treated, into a flow of the HCl gas;

b) lowering the temperature of the flow of the HCl gas to a value from −5° C. to 5° C. to form a purified HCl gas and condensates containing the methanesulfonyl chloride; and c) separating the purified HCl gas from the condensates.

4. Process for producing a hydrochloric acid solution from a HCl gas by-product of the synthesis of methanesulphonic acid, wherein methanesulphonyl chloride entrained in the HCl gas is removed, comprising:

a) injecting an amount of water ranging from 0.01 to 20%, relative to the mass of HCl to be treated, into a flow of the HCl gas;

b) lowering the temperature of the flow of the HCl gas to a value from −5° C. to 15° C. to form a purified HCl gas and condensates containing the methanesulfonyl chloride;

c) separating the purified HCl gas from the condensates.

d) combining the purified HCl gas with water to form a solution of HCl in water.

* * * * *